(12) United States Patent
Chan et al.

(10) Patent No.: US 11,766,366 B2
(45) Date of Patent: Sep. 26, 2023

(54) ABSORBENT HYGIENIC ARTICLES WITH SENSORS AND BIOCOMPOSTABLE ELEMENTS

(71) Applicant: Tethis, Inc., Raleigh, NC (US)

(72) Inventors: Ryan Nicholas Chan, Raleigh, NC (US); Gordon Sidney Cox, Durham, NC (US); Vladimiro Nettel, Kirkland (CA); James Clayton Robinson, Weddington, NC (US); Robin Weitkamp, Raleigh, NC (US)

(73) Assignee: TETHIS, INC., Raleigh, NC (US)

( * ) Notice: Subject to any disclaimer, the term of this patent is extended or adjusted under 35 U.S.C. 154(b) by 439 days.

(21) Appl. No.: 17/062,025

(22) Filed: Oct. 2, 2020

(65) Prior Publication Data

US 2021/0128368 A1    May 6, 2021

Related U.S. Application Data

(60) Provisional application No. 62/929,438, filed on Nov. 1, 2019.

(51) Int. Cl.
*A61F 13/15* (2006.01)
*A61F 13/53* (2006.01)
(Continued)

(52) U.S. Cl.
CPC ............ *A61F 13/42* (2013.01); *A61B 5/1032* (2013.01); *A61B 5/1112* (2013.01); *A61B 5/14532* (2013.01); *A61B 5/14539* (2013.01); *A61B 5/208* (2013.01); *A61B 5/4318* (2013.01); *A61B 5/7275* (2013.01); *A61B 5/746* (2013.01);
(Continued)

(58) Field of Classification Search
CPC .......... A61F 13/15; A61F 13/47; A61F 13/53; A61F 13/51; A61F 13/15203; A61F 13/5323; A61F 13/534; A61F 13/535; A61F 13/539; A61F 2013/530481; C08L 77/00; A01K 23/00; A47L 13/17
See application file for complete search history.

(56) References Cited

U.S. PATENT DOCUMENTS

| 4,590,081 A | 5/1986 | Sawada et al. |
| 5,176,669 A | 1/1993 | Klemp |

(Continued)

FOREIGN PATENT DOCUMENTS

| CN | 107028704 A | * | 5/2017 |
| JP | 6438407 B2 | * | 11/2013 |

(Continued)

*Primary Examiner* — Erich G Herbermann
*Assistant Examiner* — Ilya Y Treyger
(74) *Attorney, Agent, or Firm* — NEO IP

(57) ABSTRACT

Absorbent articles with biodegradable and/or biocompostable elements are disclosed, wherein the absorbent articles include sensors. The sensors detect and determine variables associated with collected fluids, solids, and gases, including a presence of fluids, solids, and gases, a volume of fluids, solids, and gases, and/or a distribution of fluids, solids, and gases. In one embodiment, the sensors and/or connected computing systems are calibrated to capacities and other properties of elements within the articles, including superabsorbent polymers, and are operable to trigger an alert based on detected or determined conditions.

20 Claims, 9 Drawing Sheets

(51) Int. Cl.

|     |     |     |
| --- | --- | --- |
| *A61F 13/42* | (2006.01) |
| *A61B 5/20* | (2006.01) |
| *A61B 5/00* | (2006.01) |
| *A61B 5/11* | (2006.01) |
| *A61B 5/145* | (2006.01) |
| *A61B 5/103* | (2006.01) |
| *A61F 13/84* | (2006.01) |
| *G16H 40/67* | (2018.01) |
| *G16H 50/70* | (2018.01) |
| *A61F 13/47* | (2006.01) |
| *A61F 13/51* | (2006.01) |
| *A61L 15/28* | (2006.01) |
| *A61B 10/00* | (2006.01) |

(52) U.S. Cl.
CPC ........ *A61F 13/15203* (2013.01); *A61F 13/53* (2013.01); *A61F 13/84* (2013.01); *G16H 40/67* (2018.01); *G16H 50/70* (2018.01); *A61B 10/0012* (2013.01); *A61F 2013/1513* (2013.01); *A61F 2013/1526* (2013.01); *A61F 2013/15138* (2013.01); *A61F 2013/15146* (2013.01); *A61F 2013/424* (2013.01); *A61F 2013/427* (2013.01); *A61F 2013/428* (2013.01); *A61F 2013/530481* (2013.01); *A61F 2013/8473* (2013.01); *A61F 2013/8479* (2013.01); *A61L 15/28* (2013.01)

(56) References Cited

U.S. PATENT DOCUMENTS

| | | | |
| --- | --- | --- | --- |
| 5,599,916 | A | 2/1997 | Dutkiewicz et al. |
| 6,579,231 | B1 * | 6/2003 | Phipps ................ A61B 5/0002 |
| | | | 128/920 |
| 7,459,501 | B2 | 12/2008 | Doane et al. |
| 8,044,258 | B2 | 10/2011 | Hietpas |
| 8,383,573 | B2 | 2/2013 | Dupont et al. |
| 8,461,129 | B2 | 6/2013 | Bolduc et al. |
| 8,507,607 | B2 | 8/2013 | Chambers |
| 8,563,466 | B2 | 10/2013 | Chevigny et al. |
| 8,710,212 | B2 | 4/2014 | Thibodeau et al. |
| 8,884,769 | B2 | 11/2014 | Novak |
| 8,907,155 | B2 | 12/2014 | Wang et al. |
| 10,183,094 | B2 | 1/2019 | Yamaguchi et al. |
| 10,501,920 | B2 | 12/2019 | Hird |
| 11,154,436 | B2 * | 10/2021 | Chan ................ A61F 13/15252 |
| 2004/0220538 | A1 * | 11/2004 | Panopoulos ............ A61F 13/42 |
| | | | 604/361 |
| 2005/0214541 | A1 | 9/2005 | Berrada et al. |
| 2008/0177057 | A1 | 7/2008 | Bolduc et al. |
| 2010/0057027 | A1 | 3/2010 | Furno et al. |
| 2010/0160882 | A1 | 6/2010 | Lowe |
| 2010/0179497 | A1 | 7/2010 | Brownlee |
| 2011/0152814 | A1 | 6/2011 | Seneviratne |
| 2011/0184366 | A1 | 7/2011 | Carbonari et al. |
| 2011/0319849 | A1 | 12/2011 | Collias et al. |
| 2012/0052037 | A1 | 3/2012 | Sivik et al. |
| 2012/0121519 | A1 | 5/2012 | Thomaides et al. |
| 2012/0310190 | A1 | 12/2012 | Lavon et al. |
| 2014/0309606 | A1 | 10/2014 | Richlen et al. |
| 2015/0352520 | A1 | 12/2015 | Suarez-Hemandez |
| 2017/0002098 | A1 | 1/2017 | Ayoub et al. |
| 2017/0021051 | A1 | 1/2017 | Richards et al. |
| 2017/0056253 | A1 | 3/2017 | Chester et al. |
| 2017/0224540 | A1 | 8/2017 | Li et al. |
| 2017/0281423 | A1 | 10/2017 | Panayotova et al. |
| 2018/0153746 | A1 | 6/2018 | Sookraj |
| 2018/0256412 | A1 | 9/2018 | Love |
| 2018/0289734 | A1 | 10/2018 | Benedicts et al. |
| 2018/0371309 | A1 | 12/2018 | Chan et al. |
| 2019/0111176 | A1 | 4/2019 | Sema |
| 2019/0167489 | A1 | 6/2019 | Hellmold et al. |
| 2019/0330383 | A1 | 10/2019 | Aoki et al. |
| 2020/0054782 | A1 | 2/2020 | Chan et al. |
| 2020/0138642 | A1 | 5/2020 | Wagner et al. |
| 2020/0147258 | A1 | 5/2020 | Galabura et al. |

FOREIGN PATENT DOCUMENTS

| | | |
| --- | --- | --- |
| WO | 2002074814 A1 | 9/2002 |
| WO | 2008022127 A2 | 2/2008 |
| WO | 2009012284 A1 | 1/2009 |
| WO | 2013096891 A9 | 8/2013 |
| WO | 2013180643 A1 | 12/2013 |
| WO | 2012064741 A3 | 4/2014 |

* cited by examiner

ABSORBENT HYGIENIC ARTICLES WITH SENSORS AND BIOCOMPOSTABLE ELEMENTS

CROSS REFERENCES TO RELATED APPLICATIONS

This application is related to and claims priority from the following US patents and patent applications. This application claims the benefit of U.S. Provisional Application No. 62/929,438 filed Nov. 1, 2019, which is incorporated herein by reference in its entirety.

BACKGROUND OF THE INVENTION

1. Field of the Invention

The present invention relates to absorbent hygienic articles, and more specifically relates to biocompostable absorbent hygienic articles with sensors.

2. Description of the Prior Art

It is generally known in the prior art to provide diapers, training pants, feminine hygiene products, and adult incontinence products for absorbing bodily fluids. It is also known to include elements with these articles that detect and convey when an article should be changed. For example, baby diapers often have a wetness indicator on a front of the diaper that changes colors when fluid has reached the backsheet. Recently, sensors have been applied to the outside of a backsheet that detect when an absorbent core has reached or is approaching maximum capacity.

Prior art patent documents include the following:

US Patent Publication No. 20190167489 for Smart absorbent article, components, and process of making by inventor Hellmold, et al., filed Jun. 13, 2018, and published Jun. 6, 2019, is directed to a substrate suitable for incorporation into an absorbent article for automatic detection of wetness events therein, the substrate comprising a first surface capable of being arranged proximal to a body facing side of the absorbent article and a second surface opposite said first surface and capable of being arranged proximal to a garment facing side of said absorbent article, said substrate comprising a plurality of sensor tracks disposed on said first surface and said sensor tracks comprising: at least one central track extending parallel to a length of the substrate and parallel to a longitudinal axis crossing a first end and a second end of the substrate; at least two side tracks extending parallel to the central track and oppositely arranged such that the central track extends therebetween; and wetness sensing tracks extending outboard of said two side tracks, wherein said central track, said side tracks, and said wetness sensing tracks are in electrical communication via one or more shortening elements positioned proximal to said second end and distal from said first end, and wherein the substrate is connectable to a clip-on data processing module at a position proximal to said first end and distal from said shortening elements such to form a closed electrical circuit, typically for measuring resistance and/or capacitance therethrough. In an embodiment said substrate consists of a liquid impermeable backsheet, preferably a breathable liquid impermeable backsheet.

US Patent Publication No. 20180256412 for Sensor for absorbent article by inventor Love, filed Mar. 6, 2018, and published Sep. 13, 2018, is directed to an absorbent structure, including a sensor system, can sense and measure the level of wetness contained within the absorbent structure as well as sense and measure environmental conditions. The sensor system may include passive RFID sensors or tags, RFID readers, antenna, a tuning module, a processing module, a memory module and a wireless communication module. The absorbent structure may further include two or more sensors, with a first sensor placed in a first area most likely to first be exposed to liquid and a second sensor spaced apart from the first sensor in an area likely to be exposed to liquid only after the absorbent structure has become more saturated.

U.S. Pat. No. 8,884,769 for Dimensionally-sensitive moisture sensor and an alarm system for an absorbent article by inventor Novak, filed Apr. 5, 2012, and issued Nov. 11, 2014, is directed to an apparatus and method for detecting moisture in a diaper. A moisture sensor apparatus is comprised of a housing made of material dimensionally-sensitive to moisture, such that the housing will expand or contract. Electrically conductive contacts disposed on/in the housing, are selectively coupled to, or decoupled from, each other based on a dimensional change of the sensor device when it comes into contact with moisture. An electrical signal routable through the electrically conductive contacts detects a change in state, e.g., from open to closed, and activates a local or remote alarm to indicate the presence of moisture. The consumable low-cost sensor and the optional non-metallic leads and contacts, that are at least partially biodegradable, are coupled via a convenient slidable brush connector to a resusable alarm system having optional low duty cycle transmitting capability to a receiver base station, thereby providing a cost-effective, eco-friendly and user-friendly system.

US Patent Publication No. 20100160882 for Hygiene apparatus, personal monitoring system, and method of use thereof by inventor Lowe, filed Mar. 8, 2010, and published Jun. 24, 2010, is directed to a hygiene apparatus including a housing and replaceable absorbent portion. The hygiene apparatus can include an electronic monitoring system and sensory feedback system. The absorbent portion and electronic monitoring system are retained within the housing. The electronic monitoring system includes an electronic portion which detects fluids and activates a sensory feedback signal to the user when fluids contact the system and can thereby warn the user before leakage of fluids beyond the article occurs. The user can remove and replace the absorbent cartridge accordingly. The electronic monitoring system can also include a biosensor to analyze the fluids discharged, process the analyzed information, and provide the physiological information regarding the fluids to the user. The electronic monitoring system can also transfer the information to a remote device so that the user can view the results of system's analysis.

U.S. Pat. No. 8,044,258 for Absorbent article featuring leakage warning by inventor Hietpas, filed Jun. 27, 2008, and issued Oct. 25, 2011, is directed to an absorbent article for preventing leakage including an absorbent assembly having an absorbent assembly perimeter and a leakage warning element disposed adjacent a portion of the perimeter, wherein the leakage warning element is adapted to provide a physical sensation indicating a fullness level of the absorbent assembly, and wherein the physical sensation includes an electrical impulse. Also presented is an absorbent article for providing a wearer with a warning of potential leakage, the article including an absorbent assembly and a leakage warning element disposed adjacent the absorbent assembly, wherein the leakage warning element is adapted to impart a physical sensation to the wearer, and wherein the physical sensation includes an electrical impulse.

SUMMARY OF THE INVENTION

The present invention relates to systems and methods of using sensors in biocompostable sanitary articles, including baby diapers, training pants, feminine hygiene products, and adult incontinence products as well as other biocompostable absorbent products, such as bed covers, chair covers, wound dressings, and/or other wound care absorbent products. The sensors are selected, structured, and positioned advantageously to address the challenges associated with biocompostable and biodegradable absorbent articles. Specifically, the present invention addresses challenges with determining when to change a biocompostable or biodegradable absorbent article, since consumers often do not change these products as often as is necessary to prevent leakage.

It is an object of this invention to integrate sensors within biodegradable and/or biocompostable hygienic articles to detect variables related to absorbed fluid, including a volume of fluid retention, a point at which the article has reached capacity, and/or a condition at which the article should be changed.

In one embodiment, the present invention includes a sensor system for absorbent hygienic articles including an absorbent hygienic article with biocompostable properties including an absorbent core, a sensor, and a computing device, wherein the absorbent core includes a super absorbent polymer (SAP), wherein the sensor and the computing device are in network communication, wherein the sensor is configured to detect a presence of a liquid, a solid, or a gas in the absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device, and wherein the computing device is configured to generate an alert based on the presence of the liquid, the solid, or the gas in the absorbent hygienic article and/or the properties of the liquid, the solid, or the gas of the absorbent hygienic article.

In another embodiment, the present invention includes a sensor system for absorbent hygienic articles including a sensor and a computing device, wherein the sensor and the computing device are in network communication, wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device, and wherein the computing device is configured to generate an alert based on the presence of the liquid, the solid, or the gas in the absorbent hygienic article and/or the properties of the liquid, the solid, or the gas of the absorbent hygienic article.

In yet another embodiment, the present invention includes a sensor system for absorbent hygienic articles including a sensor and an absorbent hygienic article with biocompostable properties including an absorbent core, wherein the absorbent core includes a super absorbent polymer (SAP), wherein the SAP includes an interior and surface cross-linked, charge modified polysaccharide-based biopolymer, wherein the sensor is in network communication with a computing device, and wherein the sensor is configured to detect a presence of a liquid, a solid, or gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device.

These and other aspects of the present invention will become apparent to those skilled in the art after a reading of the following description of the preferred embodiment when considered with the drawings, as they support the claimed invention.

DETAILED DESCRIPTION

Figure 1:
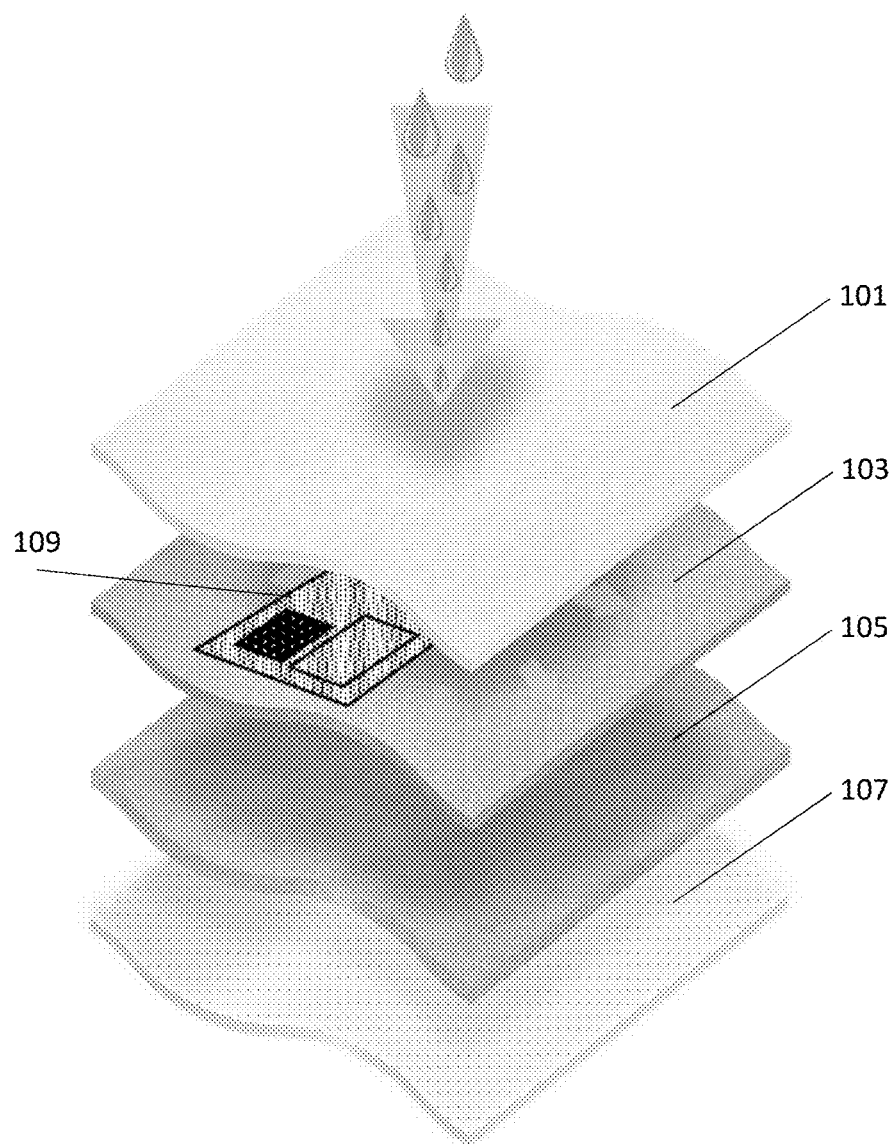
FIG. 1 illustrates an exploded view of layers of an absorbent article with a sensor according to one embodiment of the present invention.

The present invention is generally directed to systems, methods, and products for detecting variables associated with the usage of absorbent articles with biodegradable and/or biocompostable properties.

In one embodiment, the present invention includes a sensor system for absorbent hygienic articles including an absorbent hygienic article with biocompostable properties including an absorbent core, a sensor, and a computing device, wherein the absorbent core includes a super absorbent polymer (SAP), wherein the sensor and the computing device are in network communication, wherein the sensor is configured to detect a presence of a liquid, a solid, or a gas in the absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device, and wherein the computing device is configured to generate an alert based on the presence of the liquid, the solid, or the gas in the absorbent hygienic article and/or the properties of the liquid, the solid, or the gas of the absorbent hygienic article.

In another embodiment, the present invention includes a sensor system for absorbent hygienic articles including a sensor and a computing device, wherein the sensor and the computing device are in network communication, wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device, and wherein the computing device is configured to generate an alert based on the presence of the liquid, the solid, or the gas in the absorbent hygienic article and/or the properties of the liquid, the solid, or the gas of the absorbent hygienic article.

In yet another embodiment, the present invention includes a sensor system for absorbent hygienic articles including a sensor and an absorbent hygienic article with biocompostable properties including an absorbent core, wherein the absorbent core includes a super absorbent polymer (SAP), wherein the SAP includes an interior and surface crosslinked, charge modified polysaccharide-based biopolymer, wherein the sensor is in network communication with a computing device, and wherein the sensor is configured to detect a presence of a liquid, a solid, or gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device.

In one embodiment of the present invention, an absorbent hygienic article includes at least one element that is biodegradable, compostable, and/or recyclable, wherein at least some components of an absorbent core are biodegradable, compostable, and/or recyclable. In one embodiment, the elements are constructed with materials that are easily broken down by natural biodegradable or compostable processes, such as bacterial anaerobic or aerobic digestion, and wherein byproducts of the breakdown processes are non-toxic to humans. The articles include, in one embodiment, biocompostable elements, wherein the elements of the absorbent core meet ASTM standards for biocompostability, such as biocompostability as tested according to ASTM 5338, wherein 90% of a material degrades within 180 days in standard aerobic composting conditions. In another embodiment, elements of the article are between 60% and 100% biocompostable. In one embodiment, each element of the hygiene article is biocompostable. In another embodiment, each element of the hygiene article is biocompostable except for a fluid-impermeable backsheet, an adhesive, and/or additional incorporated liquid impermeable elements.

In one embodiment, the article includes at least one biocompostable and/or biodegradable superabsorbent polymer (SAP).

In one embodiment, the article includes one or more of the SAPs disclosed in U.S. patent application Ser. No. 16/592,948, filed Oct. 4, 2019, which is incorporated by reference herein in its entirety. The SAPs described in this application include biocompostable and/or biodegradable modified starch-based biopolymers. In one embodiment, the SAP is a biodegradable and/or biocompostable polysaccharide-based SAP. In one embodiment, the SAPs are crosslinked, surface treated, and/or charge-modified. Preferably, the integrated SAP exhibits between 20% and 100% degradation when compared to analytical grade cellulose in a test directed by ASTM D5338 or an equivalent biodegradation test. In another embodiment, the SAP exhibits between 50% and 95% degradation. In a further embodiment, the SAP exhibits between 60% and 85% degradation. Preferably, the bio-based carbon content of the SAP is between approximately 20% and 100%. In another embodiment, the bio-based carbon content of the SAP is between 60% and 95%.

None of the prior art discloses integration of sensors into a hygienic absorbent article in a way that specifically addresses challenges associated with biodegradable and biocompostable materials. Specifically, none of the prior art incorporates sensors into absorbent articles with biodegradable and/or biocompostable properties and provides a system operable to collect sensor data, process the data, and provide alerts, wherein the collection, processing, and generated alerts are based on calibrations, structures, and variables advantageous to biodegradable and/or biocompostable absorbent articles.

In one embodiment, an absorbent core, including an SAP, absorbent materials, and additional layers are biocompostable, biodegradable, and/or recyclable. In a further embodiment, a topsheet, the absorbent core, and any intermediate layers are biocompostable, biodegradable, and/or recyclable. In yet another embodiment, any of the layers or elements of the absorbent article are biocompostable, biodegradable, or recyclable.

Absorbent hygienic articles with biodegradable and biocompostable elements often require changing at shorter intervals than articles with non-biodegradable and non-biocompostable elements due to absorbency differences in the SAP or other materials. Advantageously, the present invention mitigates this problem by integrating sensors within the article to detect fluid and element concentrations, distributions, and content. In one embodiment, a sensor is operable to detect fluid in one or more locations of the absorbent article. In another embodiment, the sensor is operable to detect concentration or absorbency of fluid in the absorbent article. In a further embodiment, the sensor is operable to detect distribution, concentration, absorbency, and/or content of a fluid. The sensors are not limited to only determination of fluid presence and concentration but are further operable to detect material composition, distribution, temperature, volume, or other environmental, physical, or chemical variables of fecal matter, menses, or other captured bodily fluids or solids. In a further embodiment, the sensors are operable to detect and/or determine environmental variables related to an SAP, including a total volume of fluid absorbed by an SAP, a rewet absorbency, a free swell, a gel strength, and/or other factors relevant to the performance and use of an SAP.

In one embodiment, a sensor in combination with one or more local or remote computer devices (collectively, the system) is operable to detect, determine, predict, and/or calculate when an absorbent article should be changed based on the sensor data. In one embodiment, the system determines that an amount of fluid is present in the article that is greater than or equal to a preset threshold, wherein the system is operable to generate an alert to change the article. In another embodiment, the system is operable to track, store, and analyze environmental changes to determine when to generate an alert. For example, the system is operable to track a number of insults for a specific article, and they system is operable to generate an alert based on a comparison of an amount of fluid detected and/or the number of insults determined to a predefined threshold (e.g., a threshold of two insults or 80 milliliters). In one embodiment, alerts are generated at a detected volume between 20 milliliters and 200 milliliters. In another embodiment, alerts are generated at a detected volume between 75 milliliters and 165 milliliters. In a further embodiment, alerts are generated at both a detected volume between 70 milliliters and 90 milliliters and between 150 milliliters and 170 millimeters. In yet another embodiment, alerts are generated based on any of these ranges in combination with other detected variables, such as a percent distribution (e.g., percent of an article with a detected absorbed fluid), temperature (e.g., a temperature between 80° F. and 100° F.), and a weight (e.g., an increase of 0.20 pounds (0.091 kilograms)).

In one embodiment, a sensor or a system that processes the sensor data is calibrated to a specific product. Thresholds and ranges for generating an alert are manually or automatically stored, retrieved, and/or derived from a memory of the sensor, a memory of a processing computer, a remote server computer with a remote database, and/or a cloud network. For example, in one embodiment, an absorbent article includes an identification (ID) method, such as a barcode, a quick response (QR) code, or a near-field communication antenna with a preprogrammed ID, wherein an application for a computing device (e.g., a mobile phone, a desktop computer, a smartwatch) is operable to receive the ID, and based on the ID retrieve sensor calibrations, detection thresholds, and/or other product information. The application is further operable to retrieve the information based on local memory, from a remote server computer, from a cloud network, from the sensor itself (e.g., via wireless or wired communication), or from any other data source operable to store and communicate the product information. In another embodiment, the system is operable to receive and store manually set values for the product information, such as calibration data. In a further embodiment, the system is operable to store and track historical data and, based on this data, determine a volume, perceived wetness, a temperature, a percent absorption, a number of event occurrences, or other chemical, physical, or mechanical property thresholds to generate an alert. For example, in a feminine hygiene embodiment, the system is operable to generate an alert for a sanitary napkin that has reached a capacity at which previous sanitary napkins have been changed on previous cycles. In another example, the system is operable to manually or automatically determine, store, and track leaks for a baby diaper product and, based on these leak occurrences, calculate and/or determine thresholds for generating an alert before the product reaches a predicted leaking point.

Baby diapers are often constructed with at least three layers, including a top layer (a topsheet), a bottom layer (a backsheet), and an absorbent core that is positioned between the top sheet and the backsheet. One or more layers are optionally integrated within the product, such as an acquisition distribution layer (ADL) or a surge layer, wherein these intermediate layers enhance an absorption volume, a wicking rate, and/or a distribution of fluids in the article.

In one embodiment, the absorbent core is attached to the top layer and/or the back layer via physical, mechanical, or chemical means. For example, in one embodiment, the absorbent core is attached to the top layer, the back layer, or any intermediate layers via an adhesive. In another embodiment, the absorbent core is attached to the top layer, the back layer, or any intermediate layers directly via stitched, woven, or other methods of textile construction.

The top layer (e.g., topsheet) is the part of the absorbent hygiene article that comes in contact with a wearer's body (e.g., skin, hair). Notably, the top layer is referred to as the topsheet, topsheet layer, top layer, or uppermost layer and is preferably a non-woven layer. The topsheet is designed to allow fluids (e.g., urine, menses) to penetrate through the topsheet and aids in wicking moisture through the article to the absorbent core. The topsheet is generally formed from materials including, but not limited to, at least one woven material, at least one nonwoven material, at least one natural fiber, and/or at least one synthetic fiber, wherein the topsheet is produced via mechanical, chemical, or thermal means. In one embodiment, the topsheet is in contact with and/or is attached to at least one intermediate sheet, such as a transfer layer or an acquisition distribution layer (ADL), wherein the intermediate sheet provides a low-density layer that improves wicking performance. The intermediate layer further improves distribution of fluid within the non-woven core such that fluid is dispersed evenly and/or advantageously across an absorbent core. Advantageous dispersion of fluid, in one embodiment, includes distribution of the fluid to outer areas of an absorbent core, for example via physical structures such as pores, channels, creases, or varying textures. In another embodiment, the advantageous dispersion of fluid includes distribution of the fluid to outer areas and/or to inner or deeper layers of the absorbent core, for example, via physical structures such as pores, channels, creases, or varying textures. In one embodiment, the topsheet, any intermediate layers, and/or the absorbent core are sectionalized or embossed, wherein the absorbent core is constructed and arranged in patterns and shapes (e.g., embossed patterns and shapes) that draw moisture through the hygienic article in a distributed manner, such as compartmentalized triangles, squares, circles, or any variety of linear patterns. In one embodiment, the top layer is constructed from absorbent material and/or is integrated with the absorbent core, wherein the top layer is constructed from a biodegradable polymer. In another embodiment, the topsheet is constructed with the biodegradable materials described herein (e.g., including a biocompostable SAP). In one embodiment, the topsheet is impregnated with an SAP, wherein the SAP is dispersed within the topsheet. Additionally, the topsheet is operable to retain SAP particles via an outer and/or inner layer, wherein the outer and/or inner layer forms a void within the topsheet, and wherein the topsheet is optionally filled with an absorbent material, such as wood pulp fibers, cellulose fluff, or any other absorbent material known in the art of hygienic articles. The outer and/or inner layers are preferably constructed from a same material and are porous to allow wicking of moisture to the ADL and/or the absorbent core. In another embodiment, the topsheet, the ADL, the absorbent core, and/or any other layers include one or more integrated hygienic or aesthetic gels, oils, lotions, creams, or other fluid, such as antibiotic ointments, moisturizers, anti-odor agents, and/or scented products.

In one embodiment, intermediate layers have a higher absorbency than those used in traditional, non-biodegradable disposable diapers. For example, in one embodiment, an ADL has a high to medium absorbency, wherein the high absorbency is combined with an SAP that has a lower absorbency than traditional SAPs used in hygiene products. In another embodiment, the ADL is constructed with multiple sub-layers, wherein at least one layer of the ADL is operable to absorb fluid, and wherein at least one second layer of the ADL is operable to wick and distribute fluid across the absorbent article.

The ADL is, in one embodiment, constructed from non-woven materials, such as polypropylene, polyethylene, polyethylene terephthalate, or any other standard synthetic used in ADL construction. In another embodiment, the ADL is constructed from woven or non-woven biodegradable or biocompostable materials, including cotton, silk, wool, cellulose, or hemp.

Additionally and alternatively, the absorbent article includes a surge layer, as described in U.S. patent application Ser. No. 16/095,403, to inventors Park et al., which is incorporated herein by reference in its entirety, wherein the surge layer rapidly accepts and temporarily holds the liquid prior to releasing the liquid into, for instance, the fluid intake layer and/or the absorbent core. In another embodiment, the absorbent article includes an absorbent layer between a topsheet and an intermediate layer (e.g., an ADL) and includes an absorbent core beneath the intermediate layer, wherein the absorbent core includes a superabsorbent polymer.

In one embodiment, the topsheet and/or the intermediate layers include an evenly distributed superabsorbent polymer (SAP). In another embodiment, the SAP is distributed such that an outer section of the hygienic absorbent article includes a lower concentration of SAP than an inner section. In one embodiment, the SAP is distributed in channels, patterns (e.g., circles, ellipses, lines, rectangles, triangles), and/or any other ideal distribution that provides ideal absorption (e.g., anatomic distribution). In one embodiment, the absorbent article includes both a biocompostable SAP and a non-biocompostable SAP, wherein the biocompostable SAP is distributed towards an outer region of the absorbent core, and wherein the non-biocompostable SAP is distributed towards an inner region of the absorbent core. Preferably, the total SAP distribution is approximately uniform across the absorbent core. In another embodiment, the biocompostable SAP and the non-biocompostable SAP are arranged and integrated within the absorbent core in channels, patterns, and/or shapes in alternating, connected, and/or mixed manner. Alternatively, the biocompostable SAP has a higher distribution towards an inner region of the absorbent core, and a non-biocompostable SAP has a lower distribution towards an outer region of the absorbent core.

In one embodiment, the absorbent core is constructed from an absorbent material (e.g., fluff or other fibers) and a superabsorbent polymer. In another embodiment, the absorbent core includes an absorbent material, a superabsorbent polymer, and/or one or more intermediate layers that contain the absorbent materials, wick fluid across the absorbent materials, and/or provide surge or additional absorbency in the article. The core is, in one embodiment, constructed with two cores, wherein the cores are positioned laterally, and wherein the cores form a central channel that wicks fluid. In another embodiment, two or more cores are positioned in patterns and shapes to improve absorbency in an area and/or to improve fluid acquisition and distribution (e.g., through the formation of channels). In another embodiment, the cores are stacked, wherein channels, intermediate layers, and/or air space provides improved acquisition, distribution, and absorbency. In a further embodiment, the absorbent core is folded one or more times. For example, the core is folded into thirds, wherein the absorbent core forms a central, longitudinal channel. In another embodiment, the core is folded onto itself in a symmetrical or asymmetrical manner, and wherein the core forms a multi-layer core. For example, a left and a right side of the core are each folded multiple times symmetrically upon itself to form a three or six layer core. In another embodiment, the core is folded in half one or more times to create a multi-layer core. Additional folded constructions for an absorbent core can be found in U.S. patent application Ser. No. 14/634,718, to inventors Chmielewski, et al, which is incorporated herein by reference in its entirety. Notably, each of these core constructions include a superabsorbent polymer that is integrated, contained, and/or layered above, on, and/or within the absorbent core, wherein the superabsorbent polymer is preferably biocompostable and/or biodegradable.

"Curly" fibers are also considered as components of a fluffless core according to one embodiment of the present invention. Curly fibers are modified cellulose fibers, and are described in U.S. Pat. No. 6,780,201 to inventors Sun et al., which is incorporated herein by reference in its entirety.

The backsheet prevents fluids (e.g., urine, menses) from passing through the absorbent hygiene article and leaking (e.g., onto clothing, skin, etc.). The backsheet is formed from materials including, but not limited to, at least one woven material, at least one nonwoven material, and/or a polymeric and/or a thermoplastic film (e.g., polyethylene, polypropylene). In one embodiment, one or more of the at least one nonwoven material is a film-coated nonwoven material. The backsheet is generally designed to allow water vapor and air to permeate (i.e., "breathable") without allowing fluids to pass through the backsheet. In one embodiment, the backsheet is attached to the topsheet via, for example, an adhesive, stitching, or any other mechanical, physical, or chemical means known in the art. In another embodiment, the absorbent core is attached to the backsheet via any similar mechanical, physical, or chemical means.

In one embodiment, the topsheet, the backsheet, the absorbent core, and/or any intermediate layers are constructed from viscose, including fibers derived from wood pulp, bamboo, cotton, wool, silk, or any synthetic materials, including nylon, polyester. In another embodiment, the layers are constructed from rayon, spandex, Modal, or Micromodal material.

In another embodiment, the backsheet, the topsheet, or any intermediate layers are constructed with a woven material, and at least one element (e.g., the absorbent core) includes biodegradable and/or biocompostable elements. For example, in one embodiment, a removable, disposable core insert includes biodegradable and/or biocompostable wood pulp fluff as well as a biocompostable SAP, wherein the disposable core is inserted within or on top of one or more non-biodegradable or non-biocompostable woven or non-woven layers of an article. Preferably, the absorbent article includes an integrated or removable sensor within the absorbent core, between two layers, or on an exterior surface of the absorbent article (e.g., above a topsheet for contact with a user's skin or on an outside of the backsheet).

The present invention, in one embodiment, solves problems related to sustainability in the art of absorbent articles. In the diapers industry specifically, consumers are trending towards the use of reusable, cloth diapers to eliminate non-biodegradable and non-biocompostable waste. However, cloth diapers and similar products do not have the convenience of disposable diapers, and changing of biodegradable and biocompostable absorbent articles often requires more attention and/or more changes than traditional, non-biodegradable, non-biocompostable disposable articles. Thus, there is a longstanding unmet need to provide absorbent articles with biodegradable and biocompostable elements while improving the convenience and ease of use of these absorbent articles.

Referring now to the drawings in general, the illustrations are for the purpose of describing one or more preferred embodiments of the invention and are not intended to limit the invention thereto.

FIG. 1 illustrates an exploded view of layers and an embedded sensor according to one embodiment of the present invention. The layers illustrated are, in one embodiment, used in a baby diaper, wherein the layers include a topsheet 101, an acquisition distribution layer (ADL) 103, an absorbent core 105, and a backsheet 107. A sensor 109 is positioned between the ADL 103 and the topsheet 101 to identify environmental, physical, and chemical variables associated with captured content, such as an amount of fluid absorbed by the absorbent core. Notably, the positioning of the sensor 109 is not limited to a position above an ADL 103, but instead is operable to be placed on top of or below any of the layers in the article. For example, the sensor is operable to function and be positioned on an outside layer (e.g., on a backsheet or on a topsheet in contact with a user's body, skin, and/or hair) or between one or more intermediate layers (e.g., integrated within an absorbent core of the article). In another embodiment, the sensors are constructed within or as a part of a layer. For example, in one embodiment, sensing elements (e.g., wires, pads, strips) are woven into one or more layers of the absorbent article, are embedded within a non-woven material (e.g., within fibers of a non-woven), and/or are dispersed within an absorbent material (e.g., fluff, airlaid fibers, or other fiber constructions). These inter-layer sensors are operable to be constructed within any layer of the absorbent article, including a topsheet, backsheet, absorbent core, layers wrapped around a core, an ADL, and/or any other layers of an absorbent article. Alternatively, materials used in one or more layers are naturally operable to convey variable information to one or more sensors. For example, in one embodiment, a layer is constructed from naturally electrically conductive material. In one embodiment, an absorbent article does not include an ADL but instead includes a topsheet, a backsheet, an absorbent core, and a sensor positioned under the topsheet and above the absorbent core.

Sensors are operable to be constructed with any size, shape, or materials that effectively perform sensing and communication operations within the absorbent article. In one embodiment, the sensors, including the electronics and/or substrate, are biodegradable or biocompostable, such as the sensors described in U.S. Pat. Nos. 10,655,024, 10,010,272, US Patent Publication No. 2016/0193385, and/or US Patent Publication No. 2020/0008299, each of which is incorporated herein by reference in its entirety. In one embodiment, the electronics or substrate are protein-based. In one embodiment, sensors include conductivity, resistance, capacitance, ultrasound, optical, microwave, and/or any other electrical, chemical, or mechanical sensing functionality. Variables detectable by the sensors include, in one embodiment, fluid presence, fluid volume, fluid distribution, temperature, pressure, stress-strain, movement, acceleration, and conductivity-resistance, as well each of any additional variables and metrics necessary for element and composition detection, such as those collected via spectrometry or chromatography. Devices integrated within products are operable to be constructed with coverings, encasings, laminations, or other protective coatings for durability and reuse. In one embodiment, the sensors are biodegradable, biocompostable, recyclable, and/or eco-friendly. Sensors, preferably include one or more sensing capabilities within a single device or single network, wherein the sensor includes a combination of sensing elements for each variable desired, and/or wherein the sensor includes sensing elements operable to detect more than one variable. In a further embodiment, the system includes one or more sensor networks, wherein a collection of sensors or sensing elements are in network communication with one or more computing devices and/or control units. Sensors either each include individual control units or are each connected to a single control unit. Notably, sensors are operable to detect any variables associated with an absorbent article, its user, or an external environment. For example, in one embodiment, one or more temperature sensors are operable to detect a temperature external to an article, a temperature on, between, or within one or more layers, a temperature of an absorbed fluid, and/or a temperature of a user's skin or body. Sensors are further operable to detect any other variable directly or indirectly associated with the absorbent article, its environment, its user, and any absorbed materials. For example, in one embodiment, one or more sensors are operable to detect, individually or in combination, a pulse of a user, a volume of fluid absorbed, and an external temperature.

Sensors further refer to a whole, standalone product operable to sense, detect, and communicate from a single product. Sensors include at least a control unit, a sensing apparatus, and a power source, wherein the sensor is preferably portable and wireless. The control unit, in one embodiment, includes a wireless antenna for communication to one or more external devices. The wireless antenna is, in one embodiment, BLUETOOTH (including BLUETOOTH LOW ENERGY), WI-FI (including all IEEE 801.11 communication methods at 2.5 GHz, 5 GHz, 60 GHz, or otherwise), cellular (e.g., 5G, Long Term Evolution (LTE), Code-Division Multiple Access (CDMA), Enhanced Data GSM Environment (EDGE), Evolution-Data Optimized (EVDO), an/or any other digital or analog methods of communication. In one embodiment, a power source operated by a single-use battery. In another embodiment, the battery is rechargeable (e.g., a lithium-ion battery or any chemical or solid-state reusable power sources). One or more batteries are connected to one or more control units for each sensor. Sensors are operable to be in connection with the control unit directly and/or are operable to be in network communication with the control units via wired or wireless means.

In one embodiment, the system is operable to detect, communicate, and analyze a collected material, including, for example, glucose and ketone content in urine, stool, blood, or menses. In another embodiment, the sensors are operable to determine specific gravity, pH, protein, blood content, nitrite, leukocyte esterase, glucose, ketones, bilirubin, urobillnogen, color, and/or clarity. The system is operable to detect, store, track, and analyze each of these variables to develop user history model, wherein the system is further operable to use the history to determine if a variable or combination of variables is outside of a preset or normal range. For example, if a user history indicates that urine consistently exhibits a pH that is between 6.0 and 6.5, the system is operable to generate an alert to communicate that a pH is outside of a healthy range.

In a further embodiment, the absorbent article includes at least one geopositioning sensor or device and generates, tracks, and stores corresponding location data. Location data is created in the present invention using one or more hardware and/or software components. By way of example and not limitation, location data is created using satellite-based positioning systems (e.g., Global Positioning System (GPS), Differential GPS (DGPS), or Galileo), low energy Bluetooth based systems such as beacons, wireless networks such as WiFi, Radio Frequency (RF) including RF Identification (RFID), Near Field Communication (NFC), magnetic positioning, cellular triangulation, and/or combinations of these technologies. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router. Location data is communicated, stored, tracked, and analyzed on at least one device integral with the article, at least one device external to the article, a computing device in communication with one or more elements of the article, and/or one or more external servers, computers, databases, and/or cloud networks. Location data, in one embodiment, is associated with one or more user accounts or user profiles and correlated with additionally stored information, such as historical absorbent article usage data. In another embodiment, the location data is associated with one or more sensors, one or more absorbent articles, and/or one or more users. For example, in one embodiment, the system is operable to provide tracking information for a disposed article and/or an externally laundered article.

Figure 2:
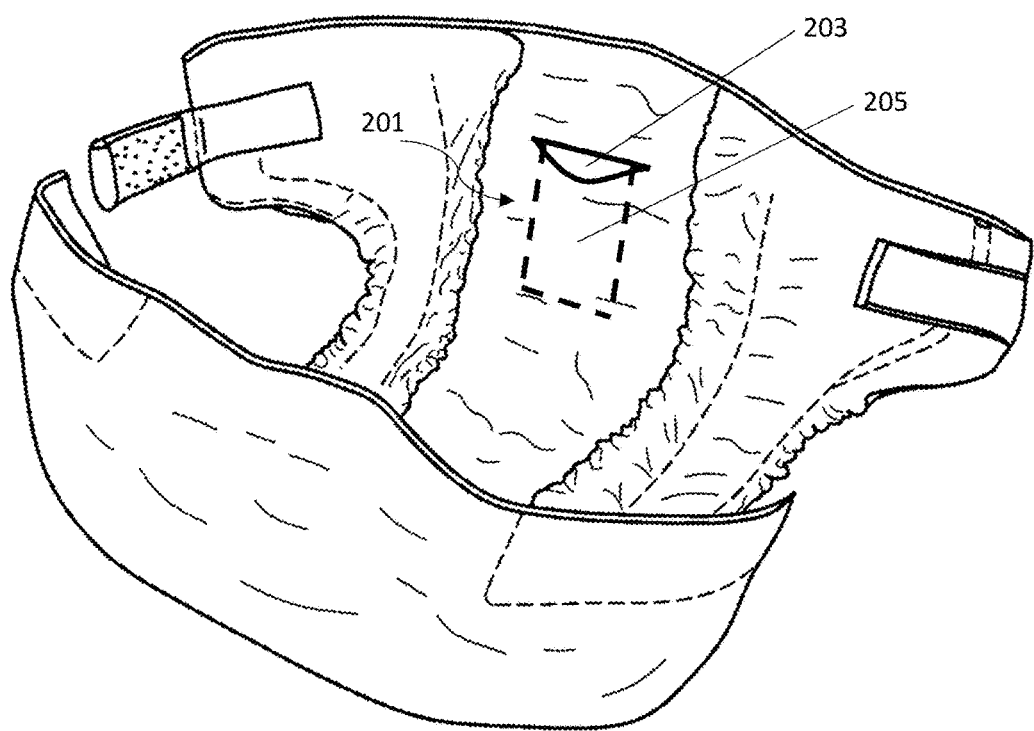
FIG. 2 illustrates a diaper with a pocket for a sensor according to one embodiment of the present invention.

FIG. 2 illustrates one embodiment of a baby diaper with a pocket 201 for incorporating a sensor. The pocket includes an internal pouch 203 and an opening 205, wherein the opening, in one embodiment, includes a snap, flap, covering, zip, latch, button, or other means of closing and securing the pocket 201. The pouch 205 is, in one embodiment, situated underneath the top layer (e.g., a topsheet) and between one or more intermediate layers. In another embodiment, the pouch is constructed on top of the top layer, wherein an inserted sensor is secured in mating contact with the top layer.

Figure 3:
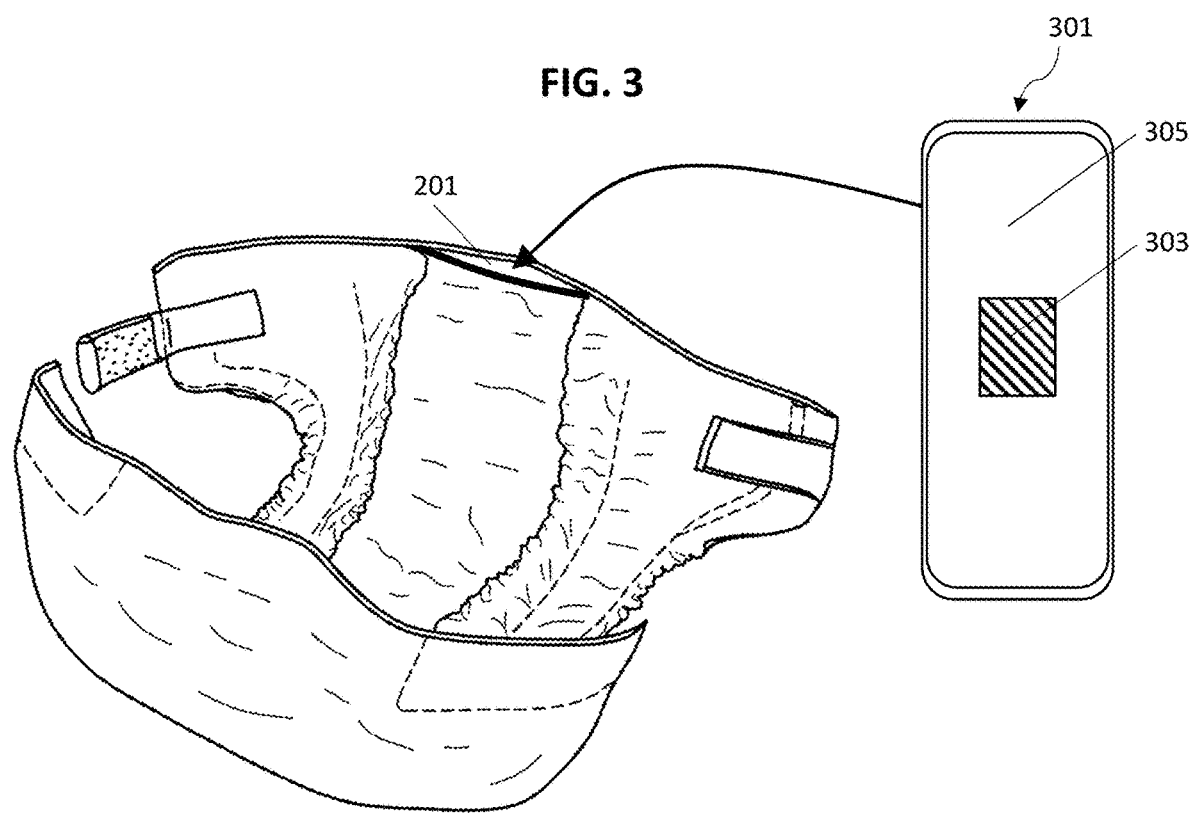
FIG. 3 illustrates a diaper with a removable absorbent insert according to one embodiment of the present invention.

FIG. 3 illustrates an insertable absorbent core 301 (or a removable absorbent insert), wherein the absorbent core 301 includes a sensor 303 and one or more layers of absorbent material 305. The sensor 303 is operable to be integrated on or within the absorbent core layers 305 and/or is removable from on or within the absorbent core layers 305. For example, in one embodiment, a sensor 303 is attached to the absorbent core 301 via a temporary adhesive, magnets, pins, friction, or other means of securing the sensor (e.g., through a pouch, slot, or embossed section), and the absorbent core 301 is inserted within the absorbent article. The sensor is further operable to be secured in any manner illustrated herein, including those described with respect to FIGS. 4A-6B The absorbent core is, in one embodiment, constructed with a natural fluff material, such as cellulose fluff or cotton. In another embodiment, the absorbent core is constructed with synthetic fluff material, such as polyester, polyethylene, or polypropylene. In a further embodiment, the core matrix is constructed from "fluffless" or alternative non-woven materials, including a web of airlaid fabric with natural or synthetic materials, which is often used in feminine hygiene products. In one embodiment, the core matrix is at least approximately 50% airlaid fabric. In another embodiment, the core matrix is at least approximately 65% airlaid fabric. In a further embodiment, the core matrix is at least approximately 85% airlaid fabric. In yet another embodiment, the core matrix is between 50% and 100% airlaid fabric, wherein between 0% and 50% of the core matrix includes an adhesive, a bonding agent, and/or a superabsorbent polymer. Bonding agents in one embodiment include resins, latex emulsions, and/or thermoplastic fibers. Preferably, the absorbent core includes one or more superabsorbent polymers (SAPs), including at least one biodegradable and/or biocompostable superabsorbent SAPs.

In one embodiment, the absorbent core 301 illustrated in FIG. 3 includes one or more intermediate layers that contain absorbent material, aid in speed of wicking, and/or aid in distribution of fluid. For example, in one embodiment, the absorbent core 301 is constructed with an encapsulating layer of non-woven fabric and is filled with wood pulp and an integrated SAP. The illustrated absorbent core 301 is removable, wherein the absorbent article includes a pouch or sleeve 201 for easy insertion and removal of the absorbent core 301. In one embodiment, an opening of the pouch or sleeve 201 is located along a front edge of the absorbent article. In another embodiment, the opening is on a side of the absorbent article, in a middle of the absorbent article, or in any other location that provides easy access and removal of the absorbent core 301. In a further embodiment, the absorbent core is attached to the diaper by way of an elastic member, adhesive, pins, buttons, or any other method of removably attaching the absorbent core 301.

Figure 4A:
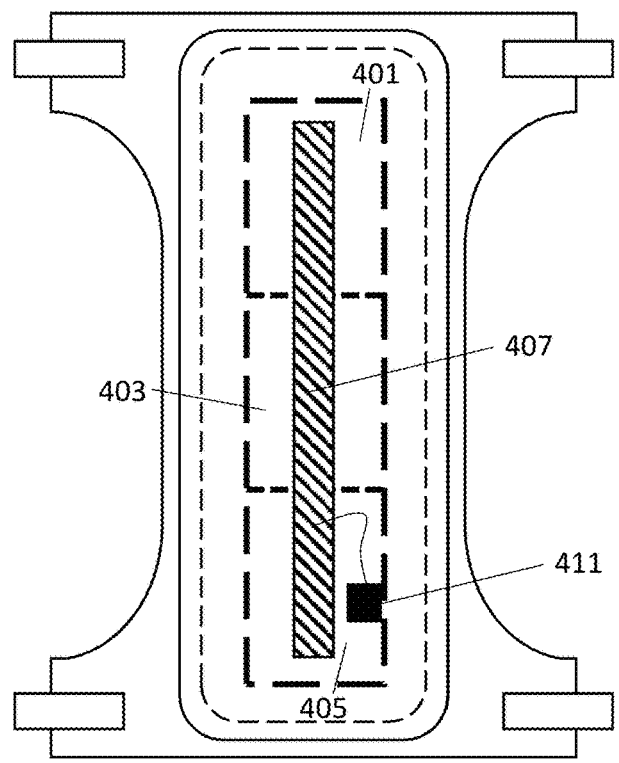
FIG. 4A illustrates an absorbent article with three zones and a full-length sensor according to one embodiment of the present invention.
Figure 4B:
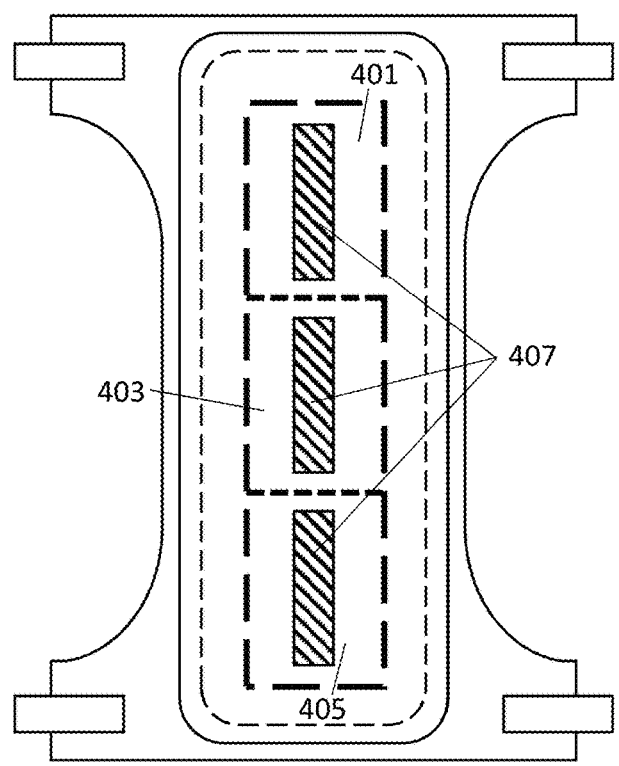
FIG. 4B illustrates an absorbent article with three zones and sensors for each of the three zones according to one embodiment of the present invention.

FIG. 4A illustrates one embodiment of sensor locations within an absorbent article, wherein the absorbent article includes a front zone 401, a middle zone 403, and a right zone 405. The absorbent article further includes a sensor 407, which, in one embodiment, extends across each of the three zones. The sensor 407 is, in one embodiment, operable to detect fluid in each of the three zones. In another embodiment, the sensor 407 detects if fluid is present in any of the three zones. The sensor 407 is connected to a control unit, wherein the control unit is operable to receive and process sensor data as well as communicate the sensor data to an external device. In a further embodiment, the sensor 407 is any sensor that is operable to detect environmental variables within the absorbent article (e.g., temperature sensor, pressure sensor, or any other chemical or mechanical sensor). FIG. 4A further illustrates a control unit 411, which is in wired network communication with the sensor. In another embodiment, the control unit is directly attached to the sensor. In a further embodiment, the control unit is wirelessly connected to the sensor. FIG. 4B illustrates another embodiment of an absorbent article with three zones, wherein each of the three zones include one or more individual sensors 407. The one or more individual sensors 407 are each connected to at least one control unit, wherein the control unit is operable to receive and process sensor data as well as communicate the sensor data to an external device. The sensors of the illustrated embodiment are operable to be positioned between, within, above, or below any layer of the absorbent article, as disclosed herein.

Figure 4C:
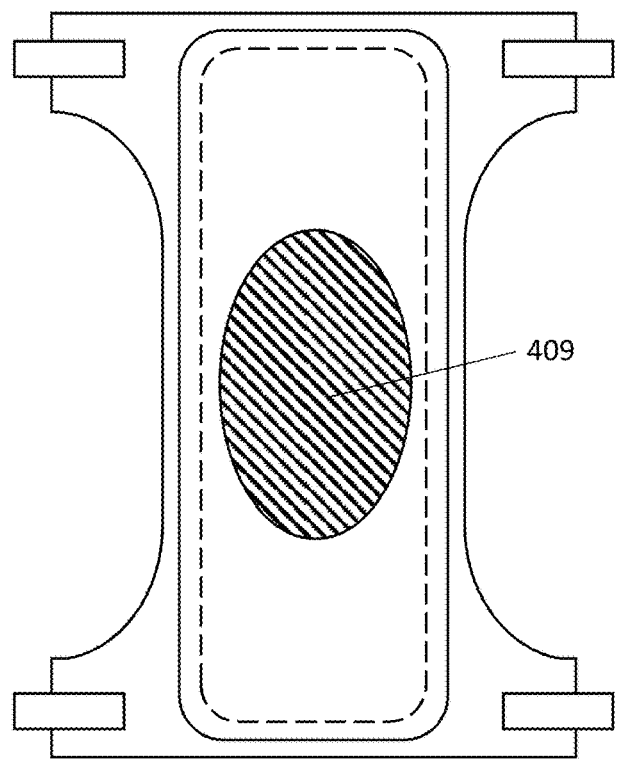
FIG. 4C illustrates an absorbent article with an elliptical sensor according to one embodiment of the present invention.
Figure 4D:
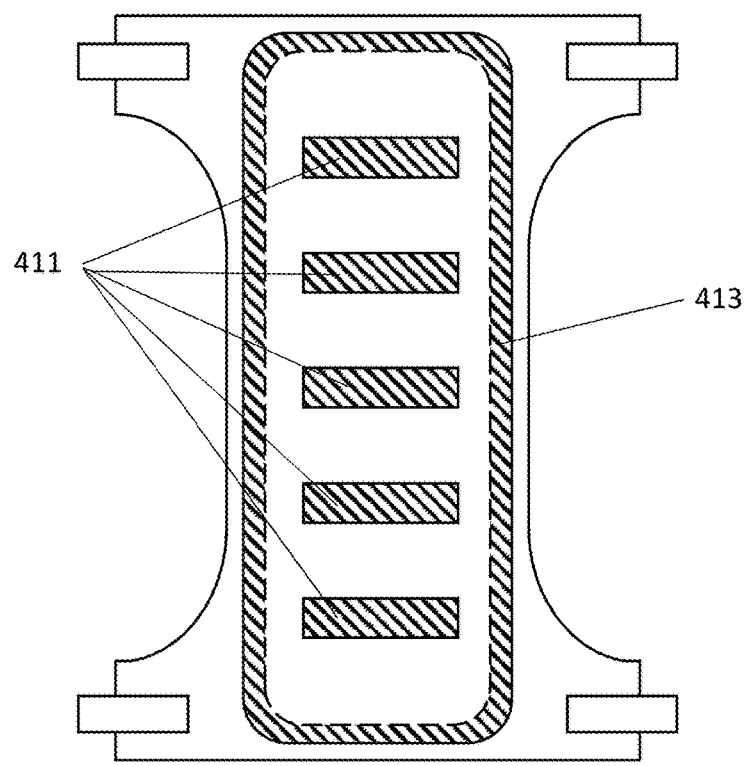
FIG. 4D illustrates an absorbent article with central and perimeter sensors according to one embodiment of the present invention.

Sensors are further operable to be positioned in any other advantageous position for detecting liquids/fluids, solids, or gases in an absorbent article. By way of example, gases detected utilizing the present invention include ammonia. FIGS. 4C and 4D illustrate alternative positions for sensors. FIG. 4C illustrates an elliptical shaped sensor 409 positioned in a middle of the absorbent article. FIG. 4D illustrates spaced sensors 411 combined with a perimeter sensor 413 to detect distribution across the absorbent article, when a leak has occurred, when a leak is imminent, and/or a quality of seal of the absorbent article to a wearer's body. In one embodiment, sensors are positioned corresponding to male or female anatomy, wherein an absorbent article constructed for female use includes a sensor positioned in a central area of the product, and wherein an absorbent article constructed for male use includes a sensor positioned in frontal area of the device. In another embodiment, a sensor is positioned in a rear area of the product for detecting variables associated with bowel movements.

Figure 5A:
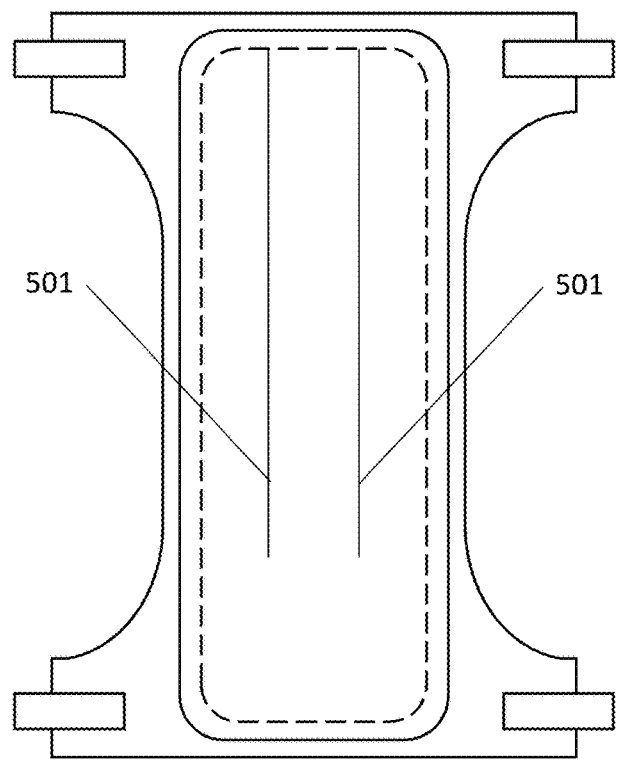
FIG. 5A illustrates an absorbent article with two sensing elements according to one embodiment of the present invention.
Figure 5B:
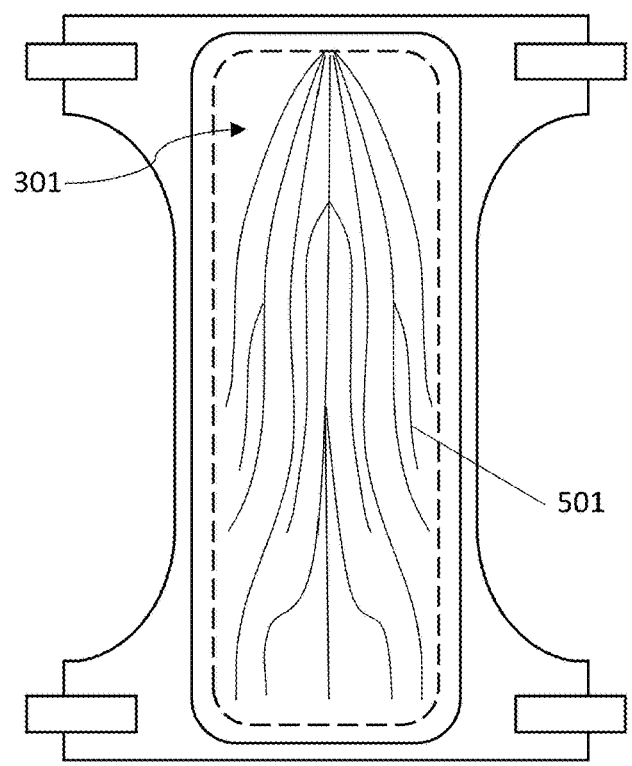
FIG. 5B illustrates an absorbent article with branching sensing elements according to one embodiment of the present invention.

FIG. 5A illustrates one embodiment of an absorbent article with two sensing elements 501, which extend along a length of the absorbent article. In one embodiment, the sensing elements 501 are connected to a control unit directly. In another embodiment, the control unit is connected via additional cables. FIG. 5B illustrates another embodiment of an absorbent article with a sensing element 501 that extends in a plurality of directions, and wherein the sensing element 501 includes at least one branch 503. In one embodiment, the control unit is connected to the sensing element 501 and is operable to detect environmental variables for each branch of the sensing element 501 (e.g., presence of fluid at each branch). In another embodiment, the sensing element determines environmental variables for the sensing element as a whole (e.g., presence of fluid at any point in the article or a total amount of fluid present in the article).

Figure 6A:
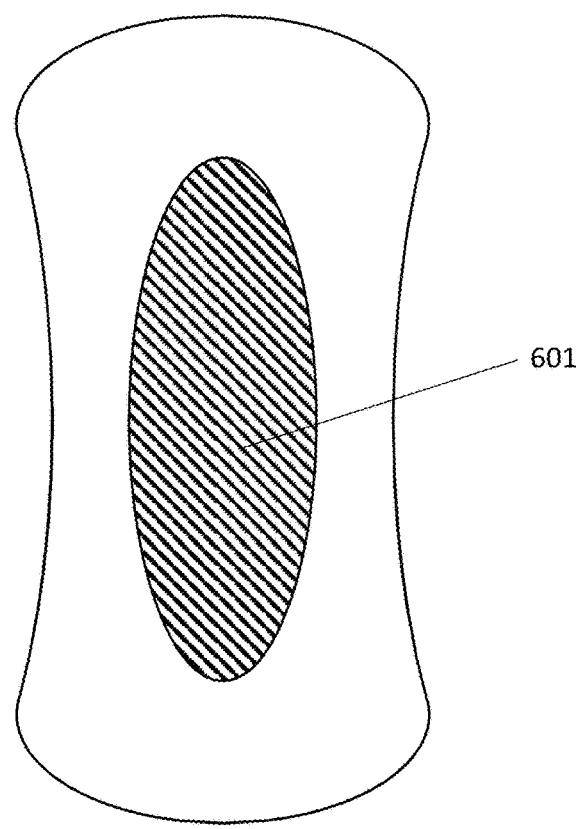
FIG. 6A illustrates a sanitary napkin with a sensor according to one embodiment of the present invention.
Figure 6B:
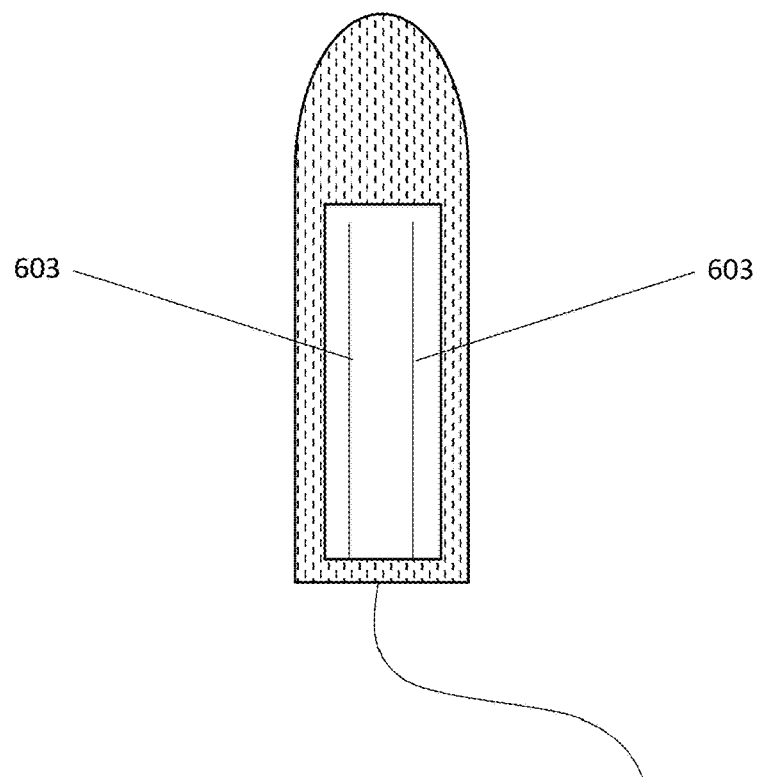
FIG. 6B illustrates a tampon with a sensor according to one embodiment of the present invention.

Notably, the absorbent articles in the disclosed embodiments are operable to be any absorbent hygienic article, including diapers, training pants, or feminine hygiene products, including sanitary napkins and tampons, as well as other biocompostable absorbent products, such as bed covers, chair covers, wound dressings, and/or other wound care absorbent products FIG. 6A illustrates a sanitary napkin with an integrated sensor 601, wherein the sensor is operable to detect at least one variable associated with menstrual cycle, including volume, temperature, color, and/or material composition of collected fluids. FIG. 6B illustrates one alternative embodiment, wherein sensor elements 603 are incorporated into a tampon. In one embodiment, the sensor elements 603 are embedded within the tampon, and a control unit communicates wirelessly with an external device. The sensor is operable to detect saturation, color, presence of specific compounds, and/or any other relevant variables known in the art.

In one embodiment, the sensor is operable to communicate with one or more external devices and systems. For example, in one embodiment, the sensor is in network communication with one or more mobile phone applications, mobile phones, desktops, desktop applications, dedicated sensor computer systems, servers, cloud networks, alarms, and/or any other external computer devices. The sensor is operable to provide real time, near-real time, periodic, or on-demand updates to the one or more external computer devices, wherein the updates include raw data from the sensor, processed data from the sensor, or alerts when certain environmental conditions have been met. For example, in one embodiment, a calibrated sensor determines that a saturation of an absorbent article has reached a sensed value. Based on the sensed value, the sensor is operable to send a push notification to an application on at least one mobile phone, wherein the push notification includes an alert that the absorbent article has reached a saturation point at which it needs to be changed. In another embodiment, the sensor is in network communication with a mobile application, which receives and processes the sensor data directly on the mobile device. For example, the mobile application is operable to determine that a temperature, saturation, and/or pressure has reached a specific level, and based on these variables, the mobile application is operable to generate an alert on the mobile device indicating that a bowl movement has occurred.

In another embodiment, the sensor is operable to process sensor information directly, wherein upon detecting that an environmental condition has been met, the sensor activates a speaker, light, or other indicator method that is directly or wirelessly connected to the device. For example, in one embodiment, a sensor is integrated into the absorbent article within an absorbent core, and an indicator device is attached to an outside of the diaper. Upon detection that an environmental condition has been met, the sensor activates the indicator device, which plays an audible alert through a built-in speaker and activates a light-emitting diode (LED) on the device.

In one embodiment, an application for a computing device (e.g., a mobile phone, personal computer, server, or cloud network) is operable to receive, store, process, analyze, and make recommendations based on raw or processed sensor data. Alternatively, the computing device includes an institutional computing device utilized in a hospital, nursing home, assisted care facility, hospice facility, etc. For example, in one embodiment, a mobile application is operable to sync event data to at least one server and at least one cloud network, wherein event data includes raw sensor data, determined bowel movements, determined urination events, an attained maximum saturation, and/or other sensed conditions. Based on this data, the server is operable to project future events, compare the trends to secondary data (e.g., diet, activity, exercise, health), generate alerts, and/or predict or determine health characteristics (e.g., by analyzing compounds, color, volume, viscosity, or other variables of urine, stool, menses, etc.).

A remote server computer, a cloud network, and/or a mobile application is operable to further receive and sync secondary health data via a mobile application, through "smart" devices (e.g., digital scales, toothbrushes, toilets, refrigerators, fitness trackers, smart watches, other devices with networking, communication, logging, and tracking capabilities). In one embodiment, the remote server computer, the cloud network, and/or the mobile application is further operable to generate graphs, charts, tables, and other trend visualizations for the sensed variables.

The system additionally includes, in one embodiment, at least one database, wherein the database is directly or remotely connected to the sensor, a computing device in direct communication with the sensor, a remote computer device, a server, and/or a cloud network. The system is operable to create and store user accounts for the data collected, including incidences of soiling, environmental variables, material properties of collected fluids and solids, analytics based on historical data, manual or automatic thresholds for products and sensors, product or sensor usage history, or any other data tracked, collected, analyzed, or generated by the system. The system is operable to provide access to the data through a mobile application, through a browser, or through any other means of receiving communicating data via a network (e.g. a local network or the Internet). In one embodiment, user accounts and user account data are protected by a number of security constraints, including password protection, encryption, abstraction, or other security protocols. In another embodiment, storage and communication of the data complies with all HIPAA regulations for storing and managing health data. Alternatively, the system is in network communication with one or more electronic health record (EHR) or electronic medical record (EMR) system for access by an individual or a medial office.

Preferably, the system is operable to provide and manage access to data for two or more user accounts. For example, the system is operable to provide a parent account, wherein the parent account is associated with data for two different children's absorbent articles. In another embodiment, a parent account is associated with data for a feminine hygiene product as well as a child's diaper. Alternatively, the system is operable to track, compare, and analyze data between two different products, wherein performance data from a first product is compared to performance data for a second product to determine products with advantageous metrics (e.g., a rate of absorption or absorbency under load), and a recommendation is communicated to a user account.

Figure 7:
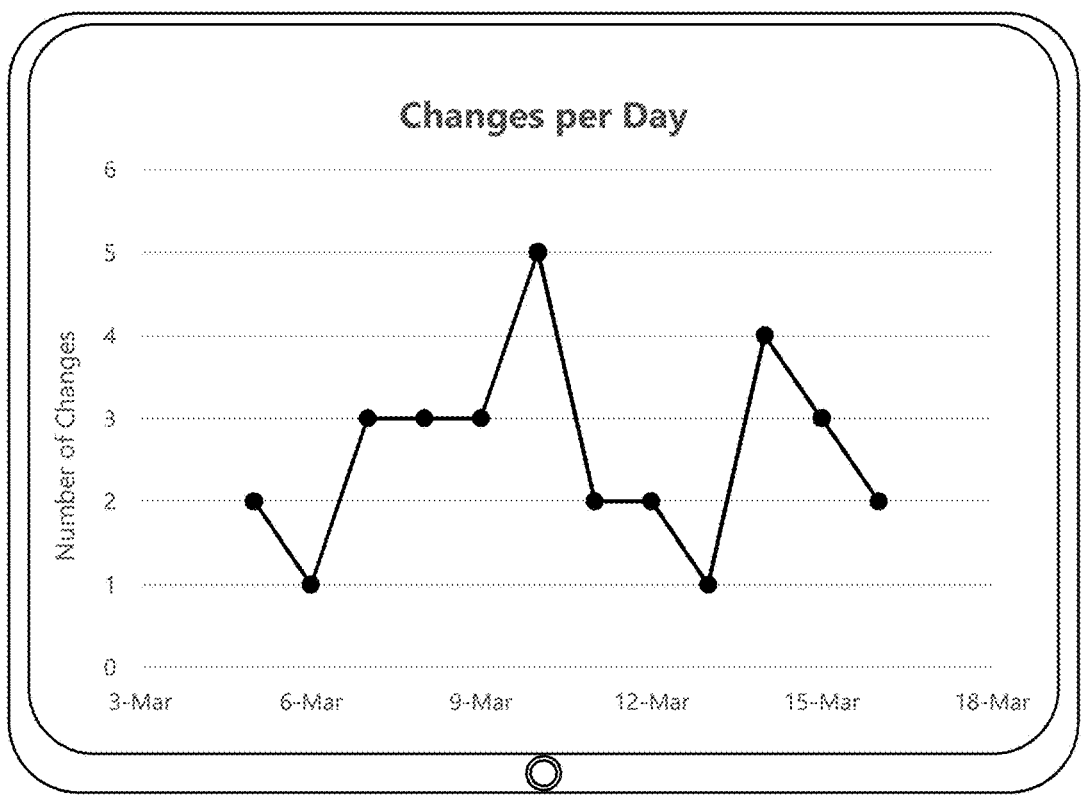
FIG. 7 illustrates a GUI with tracked absorbent article data according to one embodiment of the present invention.

FIG. 7 illustrates one embodiment of a graphical user interface (GUI), wherein an application, a remote server computer, and/or a cloud network is operable to collect information from the sensor and automatically construct a trend graph for processed data, which is then transmitted to and displayed on at least one device. In the illustrated embodiment, the system generates a visualization, which depicts a number of changes of an absorbent article per day in a line graph. Notably, data are collected from one or more sensors, applications, or databases, and the data are transformed into a visualization. For example, in one embodiment, once a sensor is manually or automatically reset, or when a sensor determines that an environmental variable is no longer present, the sensor or a remote computing device logs an article change, which is then stored in a remote database or local storage. While in the illustrated embodiment, a line graph is depicted, the graphic is operable to be any manner known in the art of data visualization, including bar charts, pie charts, scatter plots, tables, calendars, shapes, buttons, animated graphics, etc.

Figure 8A:
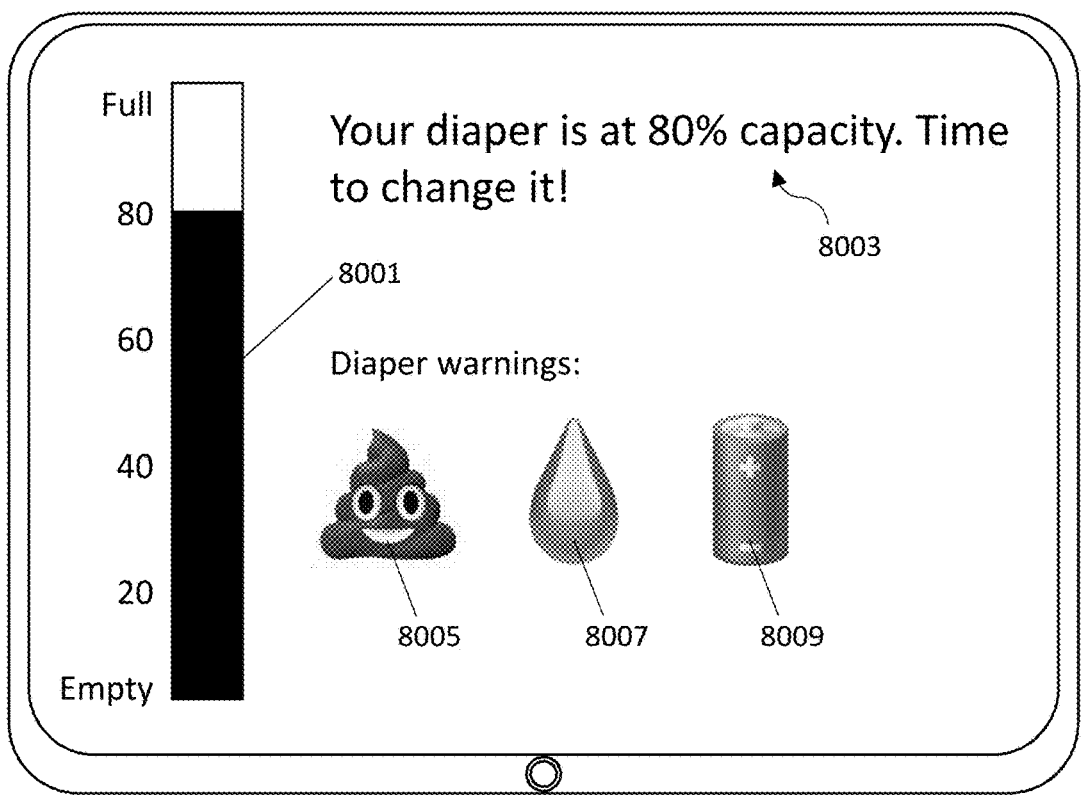
FIG. 8A illustrates an absorbent article monitoring system with warning icons according to one embodiment of the present invention.

FIG. 8 illustrates another embodiment of a GUI, wherein environmental variables from an absorbent article are displayed for a user. A meter 8001 displays a saturation level of the absorbent article, wherein data from the sensor are collected and transformed into a visualization. When an article reaches a set saturation point or other environmental condition, the sensor, a remote computer, and/or an application on a remote device is operable to display a notification to change the article or provide other information. For example, in the illustrated embodiment, once the saturation level reaches 80% capacity, the system sends a notification and/or displays a message 8003 within the application, "Your diaper is at 80% capacity. Time to change it!" Additionally, the system is operable to communicate any further detected conditions and/or warnings for the absorbent article. For example, in the illustrated embodiment, a first icon 8005 is presented to indicate that fecal matter has been detected, a second icon 8007 indicates that urine has been detected, and a third icon 8009 indicates that a battery power is running low on a sensor within the absorbent article. In another embodiment, data from this application are synchronized with a third-party service or application locally, on a remote server computer, or in a cloud network. For example, once data are collected, the data are then synchronized with a personal health tracker, such as APPLE HEALTH or are uploaded to a dedicated online service for tracking absorbent article data.

Figure 8B:
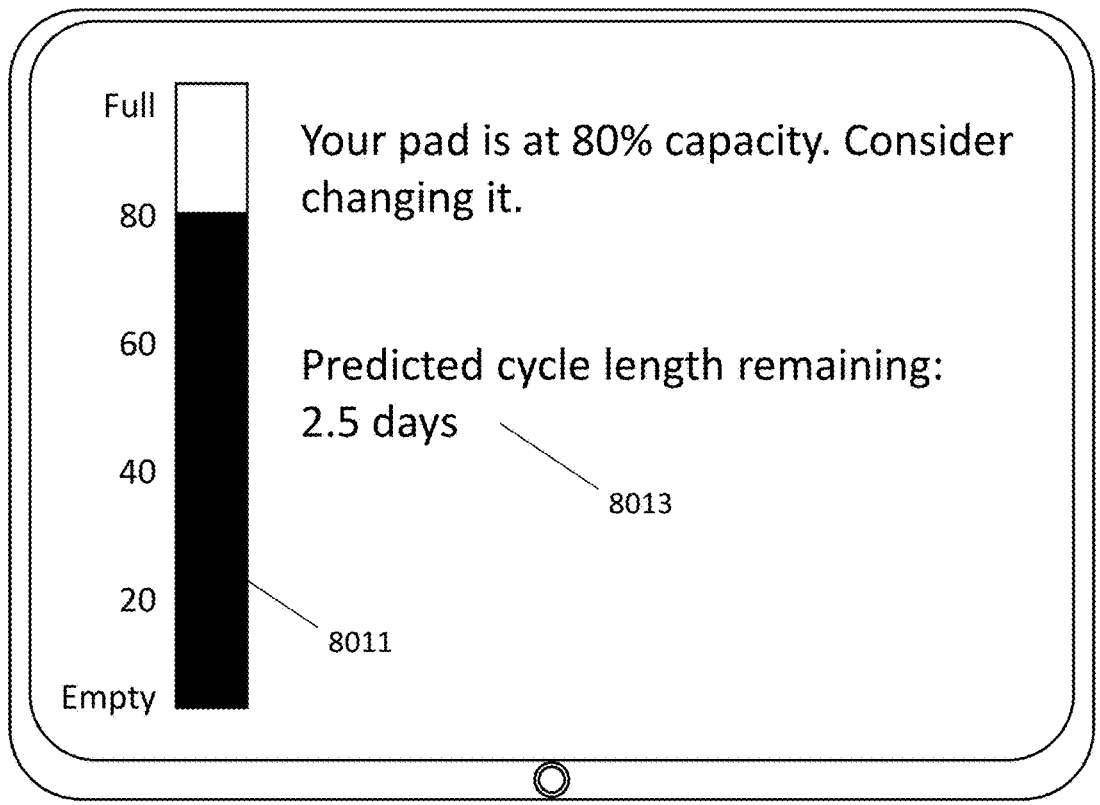
FIG. 8B illustrates a feminine hygiene monitoring system according to one embodiment of the present invention.

In another embodiment, a sanitary napkin or a tampon with integrated sensors and a computer system is operable to track, detect, predict, and communicate data for menstrual flow, blood, and/or other vaginal discharge. For example, sensors are operable to detect any numbers of variables associated with an absorbed fluid, including a volume, viscosity, color, rate of flow, and/or temperature. The sensor, an application, a remote server computer, and/or a cloud network (i.e., the system) are operable to store, track, and analyze this information and present the information to a user. In one embodiment, a user history is generated and stored locally or with a user account, wherein the history includes data, trends, and estimated future events based on the historical data. Additionally, the devices are operable to predict variables associated with the menstrual flow. In one embodiment, the historical data are used to estimate a length of when a woman's period will begin and end. For example, if a flow trend matches a predicted model for a specific time period or day, the system is operable to predict and communicate that a cycle will be complete within two days. In a further embodiment, if any variables differ significantly from a projected trendline (e.g., higher viscosity, higher flow rate, significantly different coloring), the system is operable to generate and communicate an alert to a user. FIG. 8B illustrates one embodiment of a tracking system for a menstrual cycle, wherein a capacity of a feminine hygiene product is visualized via a meter 8011, and a predicted length of a cycle is determined and displayed on the GUI.

Figure 9:
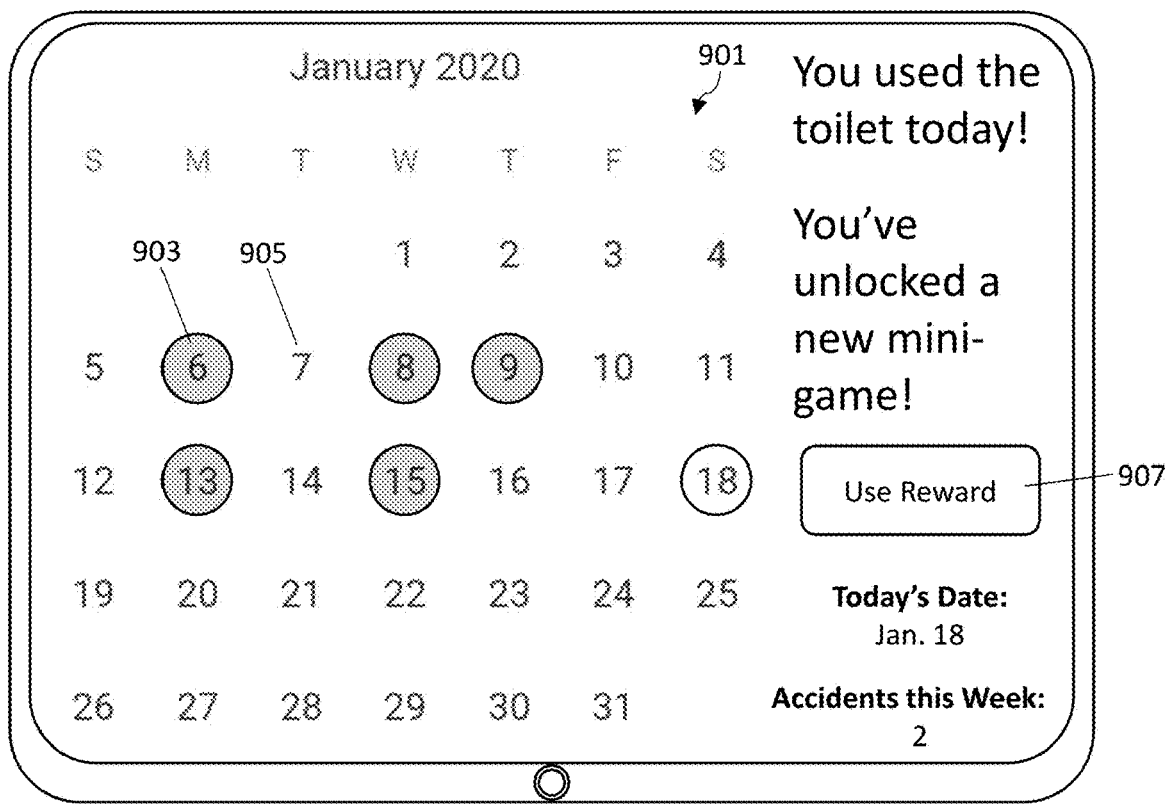
FIG. 9 illustrates a rewards system based on sensor data according to one embodiment of the present invention.

FIG. 9 illustrates a GUI displaying one embodiment of a rewards system, wherein the system is operable to track and detect soiling of absorbent articles. In the illustrated embodiment, at least one sensor is integrated into training pants, wherein the system is operable to store, track, and analyze incidents of soiled articles, and wherein the system is operable to offer rewards to a user based on an absence of soiled articles. For example, a calendar is displayed 901, wherein the calendar presents a visualization of soiling incidents. A highlighted day 903 indicates an incidence of soiling, and a non-marked day 905 indicates a non-soiling event. In one embodiment, highlighted days visualize days that the system detects that an absorbent article has been removed from a user's body, indicating that a user has used a toilet instead of the absorbent article. In another embodiment, detection of absorbent article removal is paired with one or more additional data sources, such as sensors attached to a toilet and/or automatic or manual logging of toilet usage.

The system is operable to automatically set goals or rewards and/or receive goals or rewards from an account (e.g., an administrator account or a parent account). In one embodiment, the system adjusts points amounts for one or more user accounts based on determined or logged usages of a toilet or based on set time periods elapsed without soiling an absorbent article (e.g., hours, days, weeks). For example, in one embodiment, a day without a detected soiling adds a point to a user account, wherein the system is operable to receive an indication of redemption of the points, and wherein the system is operable to provide a reward based on the redemption. Reward examples include access to media (e.g., videos, photos, music), access to a game, currency conversion (e.g., points to fiat currency, cryptocurrency, digital currency, virtual currency), and/or access to an electronic device for a preset amount of time (e.g., 1 hour of unrestricted access to a smartphone or tablet). In another embodiment, the system allows direct awarding of rewards and incentives instead of points. For example, in the illustrated embodiment, a detected or determined usage of a toilet unlocks a digital game, wherein the system presents a button 907 for redemption of the reward. In another embodiment, points are instead grades, badges, levels, or other metrics.

The system is operable to store, manage, or track rewards system on the sensor, on a computing device, on a remote server computer, or on a cloud network for one or more user accounts. In one embodiment, an application on a device provides a GUI for managing and interacting with the rewards system, wherein one or more user accounts are operable to access the rewards system through the application. In another embodiment, the system includes a second application or a second user account (e.g., an administrator account or a parent account), wherein the second application or the second user account is operable to track, manage, view, and set rewards and goals for one or more additional user accounts. For example, the system is operable to receive from a parent account a set of goals for a first user account (e.g., one week without a soiled absorbent article and an indication of a first user account) and associate the set of goals with the first user account in a database of the system, and wherein the system is also operable to receive from the parent account a second set of goals for a second user account (e.g., two days in a row using the toilet and a username of a second user account) and associate the second set of goals with the second user account in a database of the system. In a further embodiment, goals, rewards, point totals, and other elements of the reward system are operable to be set or requested by a user account directly.

Figure 10:
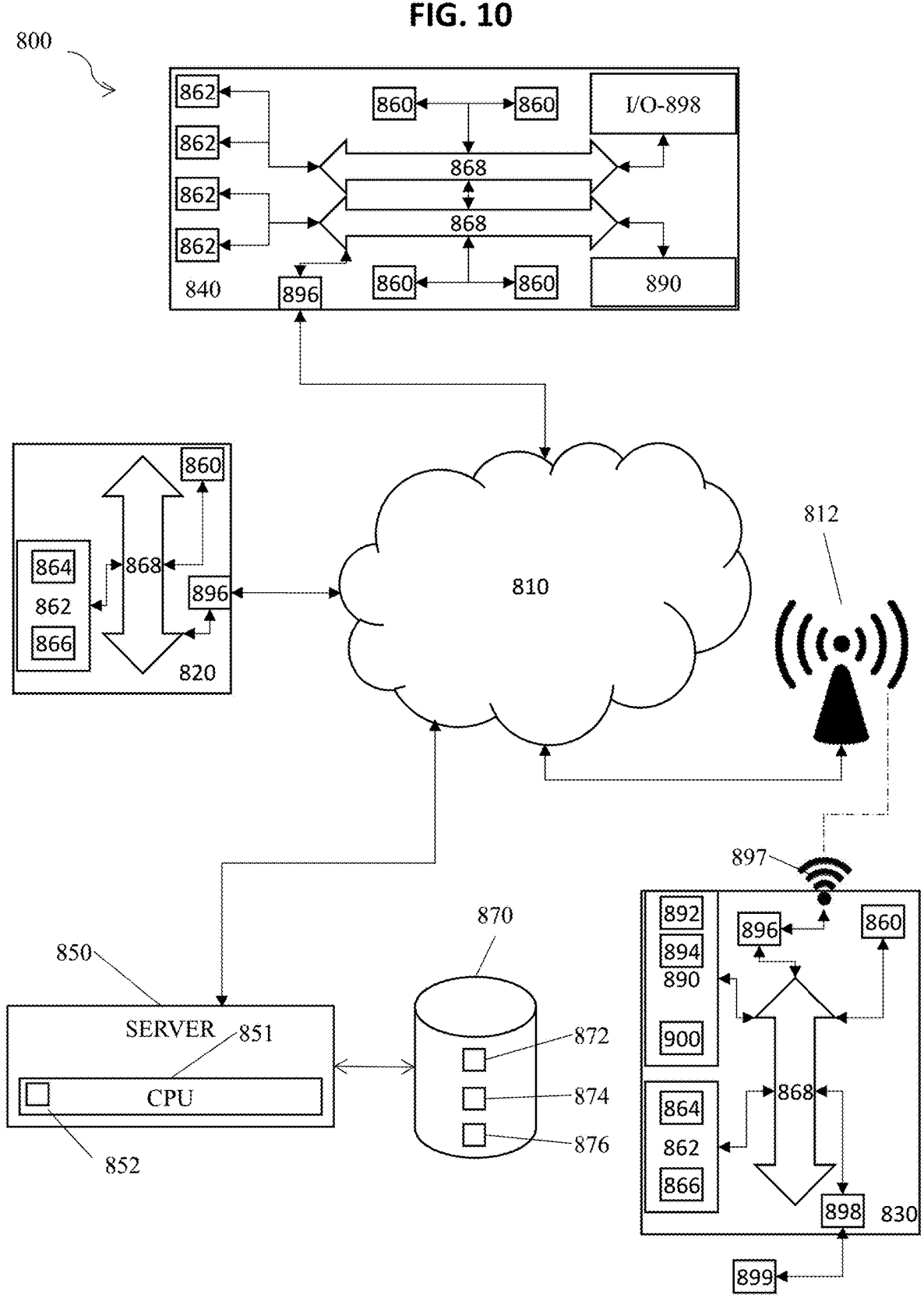
FIG. 10 is a schematic diagram of a cloud-based system of the present invention.

FIG. 10 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 10, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 10, may include other components that are not explicitly shown in FIG. 10, or may utilize an architecture completely different than that shown in FIG. 10. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

What it claimed is:

1. A sensor system for absorbent hygienic articles comprising:
   an absorbent hygienic article with biocompostable properties including an absorbent core;
   a sensor; and
   a computing device,
   wherein the absorbent core includes a super absorbent polymer (SAP);
   wherein the sensor and the computing device are in network communication;
   wherein the sensor is configured to detect a presence of a liquid, a solid, or a gas in the absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device;
   wherein the computing device is configured to generate an alert based on the presence of the liquid, the solid, or the gas in the absorbent hygienic article and/or the properties of the liquid, the solid, or the gas of the absorbent hygienic article; and
   wherein the computing device is configured to receive a variable including glucose content, ketone content, specific gravity, protein content, blood content, nitrite content, leukocyte esterase content, bilirubin content, and/or urobillnogen content of the liquid or the solid and/or an ammonia content of the gas from the sensor or from at least one database, wherein the computing device is further configured to develop a history model for a user associated with the sensor, wherein the computing device is further configured to use the history model to determine if the variable is outside a normal range of the variable of the history model, and wherein the computing device is configured to generate the alert if the variable is outside the normal range of the variable of the history model.

2. The system of claim 1, wherein the computing device is configured to determine, based on data received from the sensor about the liquid, the solid, or the gas, a percent absorption of the liquid or the solid by the absorbent hygienic article and/or a number of liquid distribution events, solid distribution events, or gas distribution events.

3. The system of claim 1, wherein the computing device is configured to determine a threshold for generating the alert based on data from the sensor obtained from a second absorbent hygienic article, wherein the data from the sensor obtained from the second absorbent hygienic article corresponds to at least one past leak occurrence.

4. The system of claim 1, wherein the sensor is biodegradable.

5. The system of claim 1, further comprising at least one geopositioning component, wherein the at least one geopositioning component generates location data for the sensor and/or the absorbent hygienic article.

6. The system of claim 1, wherein the SAP includes an interior and surface crosslinked, charge modified polysaccharide-based biopolymer, and wherein the biobased carbon content of the interior and surface crosslinked, charge modified polysaccharide-based biopolymer is at least approximately 80%.

7. The system of claim 1, wherein the absorbent hygienic article includes at least three zones, and wherein the sensor is configured to detect the presence of the liquid, the solid, or the gas and/or the properties of the liquid, the solid, or the gas in each of the at least three zones separately from the other zones of the at least three zones.

8. The system of claim 1, wherein the sensor is further configured to detect an imminency of a leak of the liquid or the solid from the absorbent hygienic article.

9. The system of claim 1, wherein the sensor is further configured to detect a quality of a seal of the absorbent hygienic article to a body of a user of the absorbent hygienic article.

10. The system of claim 1, wherein the sensor is further configured to detect at least one variable associated with a menstrual cycle, wherein the at least one variable includes a color, a saturation, and/or a material composition of the liquid.

11. A sensor system for absorbent hygienic articles comprising:
  a sensor; and
  a computing device,
  wherein the sensor and the computing device are in network communication;
  wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device;
  wherein the computing device is configured to generate an alert based on the presence of the liquid, the solid, or the gas in the absorbent hygienic article and/or the properties of the liquid, the solid, or the gas of the absorbent hygienic article; and
  wherein the computing device is configured to synchronize data obtained from the sensor with another application on the computing device or another application on a separate computing device.

12. The system of claim 11, wherein the computing device includes a graphical user interface (GUI), wherein the GUI is configured to display a notification that fecal matter has been detected by the sensor and/or a notification that urine has been detected by the sensor.

13. The system of claim 11, wherein the computing device is configured to analyze data from the sensor to estimate an end date for a menstrual cycle based on historical data.

14. The system of claim 11, wherein the computing device is configured to develop a history model for a user associated with the sensor, wherein the computing device is further configured to use the history model to determine if a variable measured by the sensor is outside a normal range of the variable of the history model, and wherein the computing device is further configured to generate the alert if the variable is outside the normal range of the variable of the history model.

15. A sensor system for absorbent hygienic articles comprising:
  a sensor; and
  an absorbent hygienic article with biocompostable properties including an absorbent core;
  wherein the absorbent core includes a super absorbent polymer (SAP);
  wherein the SAP includes an interior and surface cross-linked, charge modified polysaccharide-based biopolymer;
  wherein the sensor is in network communication with a computing device;
  wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device; and
  wherein the absorbent hygienic article includes at least three zones, and wherein the sensor is configured to detect the presence of the liquid, the solid, or the gas and/or the properties of the liquid, the solid, or the gas in each of the at least three zones separately from the other zones of the at least three zones.

16. The system of claim 15, wherein the sensor is configured to detect distribution of the liquid, the solid, or the gas within the absorbent hygienic article.

17. The system of claim 15, wherein the absorbent hygienic article includes a pocket configured to receive the sensor, wherein the pocket includes a closeable opening.

18. A sensor system for absorbent hygienic articles comprising:
  an absorbent hygienic article with biocompostable properties including an absorbent core;
  a sensor; and
  a computing device,
  wherein the absorbent core includes a super absorbent polymer (SAP);
  wherein the sensor and the computing device are in network communication;
  wherein the sensor is configured to detect a presence of a liquid, a solid, or a gas in the absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device;
  wherein the computing device is configured to generate an alert based on the presence of the liquid, the solid, or the gas in the absorbent hygienic article and/or the properties of the liquid, the solid, or the gas of the absorbent hygienic article; and
  wherein the absorbent hygienic article includes at least three zones, and wherein the sensor is configured to detect the presence of the liquid, the solid, or the gas and/or the properties of the liquid, the solid, or the gas in each of the at least three zones separately from the other zones of the at least three zones.

19. A sensor system for absorbent hygienic articles comprising:
  a sensor; and
  a computing device,
  wherein the sensor and the computing device are in network communication;
  wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device;
  wherein the computing device is configured to generate an alert based on the presence of the liquid, the solid, or the gas in the absorbent hygienic article and/or the properties of the liquid, the solid, or the gas of the absorbent hygienic article; and
  wherein the computing device is configured to analyze data from the sensor to estimate an end date for a menstrual cycle based on historical data.

20. A sensor system for absorbent hygienic articles comprising:
  a sensor; and
  a computing device,
  wherein the sensor and the computing device are in network communication;

wherein the sensor is configured to detect a presence of a liquid, a solid, or a gas in an absorbent hygienic article and/or properties of the liquid, the solid, or the gas in the absorbent hygienic article and communicate the presence of the liquid, the solid, or the gas in the absorbent hygienic article and/or the properties of the liquid, the solid, or the gas in the absorbent hygienic article to the computing device;

wherein the computing device is configured to generate an alert based on the presence of the liquid, the solid, or the gas in the absorbent hygienic article and/or the properties of the liquid, the solid, or the gas of the absorbent hygienic article; and wherein the computing device is configured to develop a history model for a user associated with the sensor, wherein the computing device is further configured to use the history model to determine if a variable measured by the sensor is outside a normal range of the variable of the history model, and wherein the computing device is further configured to generate the alert if the variable is outside the normal range of the variable of the history model.

* * * * *